(12) United States Patent
Lee et al.

(10) Patent No.: US 8,689,795 B2
(45) Date of Patent: Apr. 8, 2014

(54) TEMPOROMANDIBULAR JOINT BALANCING APPLIANCE AND METHOD FOR USING THE SAME

(75) Inventors: Young-Jun Lee, Cheonan (KR); Hwa-Jeong Lee, Cheonan (KR); Kyung-Hoon Lee, Cheonan (KR)

(73) Assignee: Jinbiotech Co., Ltd., Cheonan (KR)

( * ) Notice: Subject to any disclaimer, the term of this patent is extended or adjusted under 35 U.S.C. 154(b) by 951 days.

(21) Appl. No.: 12/705,406

(22) Filed: Feb. 12, 2010

(65) Prior Publication Data
US 2010/0288290 A1   Nov. 18, 2010

(30) Foreign Application Priority Data
May 18, 2009   (KR) .................. 10-2009-0043112

(51) Int. Cl.
| | |
|---|---|
| *A61F 5/37* | (2006.01) |
| *A61F 13/00* | (2006.01) |
| *A61F 11/00* | (2006.01) |
| *A61C 5/14* | (2006.01) |
| *A61C 3/00* | (2006.01) |
| *A61C 19/04* | (2006.01) |
| *A61C 9/00* | (2006.01) |

(52) U.S. Cl.
USPC ........... 128/861; 128/846; 128/848; 128/857; 128/862; 433/6; 433/7; 433/18; 433/19; 433/24; 433/68; 433/69; 433/70; 433/71; 602/902

(58) Field of Classification Search
USPC ................ 128/846, 848, 857, 862, 859, 861; 433/6, 7, 18, 19, 24, 68–71; 602/902
See application file for complete search history.

(56) References Cited

U.S. PATENT DOCUMENTS

| | | | | |
|---|---|---|---|---|
| 5,267,862 | A * | 12/1993 | Parker ......................... | 433/215 |
| 5,624,257 | A   | 4/1997  | Farrell | |
| 8,235,052 | B2 * | 8/2012 | Maurello ...................... | 128/859 |
| 2008/0295850 | A1 * | 12/2008 | Lesniak ........................ | 128/862 |
| 2011/0100379 | A1 * | 5/2011  | Doctors et al. ................ | 128/862 |

FOREIGN PATENT DOCUMENTS

| | | |
|---|---|---|
| KR | 1020080103287 A | 11/2008 |
| WO | WO 2006/108209 A1 | 10/2006 |

\* cited by examiner

*Primary Examiner* — Patricia Bianco
*Assistant Examiner* — Brandon L Jackson

(57) ABSTRACT

A TemporoMandibular Joint (TMJ) balancing appliance and a method for using the same are provided, in which a first base portion accommodates incisor teeth, a second base portion is extended from a left side of the first base portion and accommodates left molar teeth, and a third base portion is extended from a right side of the first base portion and accommodates right molar teeth. The first base portion includes an upper part for accommodating upper incisor teeth and a lower part for accommodating lower incisor teeth and has a center for accommodating the upper and lower incisor teeth higher than the left and right sides.

16 Claims, 14 Drawing Sheets

(a)　　　　　　　　(b)　　　　　　　　(c)

(a)

(b)

TEMPOROMANDIBULAR JOINT BALANCING APPLIANCE AND METHOD FOR USING THE SAME

CROSS-REFERENCE TO RELATED PATENT APPLICATION

This application claims the benefit under 35 U.S.C. §119 (a) of a Korean Patent Application filed in the Korean Intellectual Property Office on May, 18, 2009 and assigned Serial No. 10-2009-0043112, the entire disclosure of which is hereby incorporated by reference.

BACKGROUND OF THE INVENTION

1. Field of the Invention

The present invention relates generally to a temporomandibular joint balancing appliance and a method for using the same and, more particularly, to a temporomandibular joint balancing appliance, which eliminates a temporomandibular joint imbalance caused by an external impact, unilateral chewing, stress, etc., induces relaxation of muscles related to the temporomandibular joint, and activate circulation of cerebrospinal fluid, and a method for using the same.

2. Description of the Related Art

A TemporoMandibular Joint (TMJ) is a ginglymoarthrodial joint, referring to its dual compartment structure, which serves as a central axis of mouth opening and closing movements and mandibular movements. The TMJ makes a rotational movement and a gliding movement and plays a significant role in chewing and talking. The TMJ has an upper temporal bone and a lower jaw bone called a mandible.

The TMJ is an essential part of the body in which nine of 12 cranial nerves are extended and a large number of blood vessels, lymphatic vessels, and nerves are distributed. A TMJ imbalance is a cause of subluxation of the upper cervical spine and breaches the balance of muscles related to the TMJ, thereby causing a wide range of general syndromes including disorders in the central nervous system and the spine and joints, headache, dizziness, circulation disorders, otolaryngological disorders, urologic disorders, respiratory disorders, and growth disorders.

This TMJ imbalance is caused by an external impact, unilateral chewing, teeth grinding, stress, and a daily activity like saliva swallowing.

Therefore, the importance of the TMJ is increasing and the TMJ is under active study and research. Also, many TMJ protection appliances have been invented, such as a TMJ correction pad or mouthpiece, a correction device, etc.

Conventional technologies disclosed in U.S. Pat. No. 5,259,762 entitled "Oral Appliance" and U.S. Pat. No. 5,624,257 entitled "Oral Appliance" are characterized in that a base portion for receiving the teeth of the upper and lower jaws is integrally formed to a uniform height. Thus they have limitations in eliminating a TMJ imbalance and do not take into account individuals' different TMJ imbalances. Hence, although the conventional technologies may protect the TMJ by inserting a cushioning device of a predetermined height between the teeth and thus mitigating an impact on the teeth, they do not eliminate a TMJ imbalance. Therefore, the effects of the conventional technologies are limited and are ineffective in solving TMJ imbalance-incurred problems. Moreover, the conventional oral appliances are designed such that it is impossible to eliminate individuals' different TMJ imbalances structurally.

In the conventional oral appliances, opposite sides for accepting molar teeth are thicker than a top side for accepting incisor teeth to mitigate an impact produced from the molar teeth part. This design makes the incisor teeth touch the base portion earlier than molar teeth, thus reducing the shock mitigation effect of the molar teeth part. Thus, the TMJ imbalance is difficult to overcome.

In addition, the conventional oral appliances have outer and inner flange portions along the base portion to prevent teeth misalignment and enhance fixation strength. However, the outer and inner flange portions regulate even natural teeth movements, thus causing severe teeth pain, when the oral appliances are worn. Especially, upper and lower channels are designed at the same level at the top side of the base portion, thus disturbing normal incisor occlusion and increasing pain.

SUMMARY OF THE INVENTION

An aspect of exemplary embodiments of the present invention is to address at least the problems and/or disadvantages and to provide at least the advantages described below. Accordingly, an aspect of exemplary embodiments of the present invention provides a TMJ balancing appliance that is inserted between teeth, for balancing a TMJ and thus minimizing TMJ imbalances, and a method for using the TMJ balancing appliance.

Another aspect of exemplary embodiments of the present invention provides a TMJ balancing appliance having second and third base portions with controllable heights for accommodating molar teeth, which can be fabricated according to the teeth structure of an individual user, eliminate individuals' different TMJ imbalances, and control a TMJ balance accurately, and a method for using the TMJ balancing appliance.

Another aspect of exemplary embodiments of the present invention provides a TMJ balancing appliance in which second and third base portions for accommodating molar teeth are designed to be higher than a first base portion so that molar teeth parts being a core of a TMJ balance contact the second and third base portions earlier, thereby minimizing a TMJ imbalance, and a method for using the TMJ balancing appliance.

A further aspect of exemplary embodiments of the present invention provides a TMJ balancing appliance in which a first base portion is inclined in order to achieve normal occlusion of incisor teeth, when the appliance is worn, and in which a lower start point of the first base portion is behind an upper start point of the first base portion in order to increase a comfortable wearing feeling of a user, and a method for using the TMJ balancing appliance.

In accordance with an aspect of exemplary embodiments of the present invention, there is provided a TMJ balancing appliance, in which a first base portion accommodates incisor teeth, a second base portion is extended from a left side of the first base portion and accommodates left molar teeth, and a third base portion is extended from a right side of the first base portion and accommodates right molar teeth. The first base portion includes an upper part for accommodating upper incisor teeth and a lower part for accommodating lower incisor teeth and has a center for accommodating the upper and lower incisor teeth higher than the left and right sides.

In accordance with another aspect of exemplary embodiments of the present invention, there is provided a TMJ balancing appliance in which a first base portion has an upper part for accommodating upper teeth and a lower part for accommodating lower teeth, a center of the upper and lower parts for accommodating upper and lower incisor teeth being higher than sides of the first base portion, a second base portion is extended from a left side of the first base portion and accommodates left molar teeth, and a third base portion is extended from a right side of the first base portion and accommodates right molar teeth. The first base portion has an outer wall formed along an outer rim of the first base station, and an inner wall formed along an inner rim of the first base station and the outer wall is higher than the inner wall.

In accordance with a further aspect of exemplary embodiments of the present invention, there is provided a method for using a TMJ balancing appliance, in which a left balancing body to be inserted between left molar teeth is generated, a right balancing body to be inserted between right molar teeth is generated, the left and right balancing bodies are inserted between the left molar teeth and between the right molar teeth, shapes of incisor teeth are molded on a first base portion filled with a teeth fixing material, the first base portion having the shapes of the incisor teeth molded therein is combined with second and third base portions, and shapes of the other teeth are molded on the second and third base portions filled with the teeth fixing material using the first base portion having the shapes of the incisor teeth molded therein.

BRIEF DESCRIPTION OF THE DRAWINGS

The above and other objects, features and advantages of certain exemplary embodiments of the present invention will be more apparent from the following detailed description taken in conjunction with the accompanying drawings, in which.

Throughout the drawings, the same drawing reference numerals will be understood to refer to the same elements, features and structures.

DETAILED DESCRIPTION OF EXEMPLARY EMBODIMENTS

The matters defined in the description such as a detailed construction and elements are provided to assist in a comprehensive understanding of exemplary embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

With reference to FIGS. 1 to 10, a TemporoMandibular Joint (TMJ) balancing appliance according to exemplary embodiments of the present invention will be described in detail.

Figure 1:
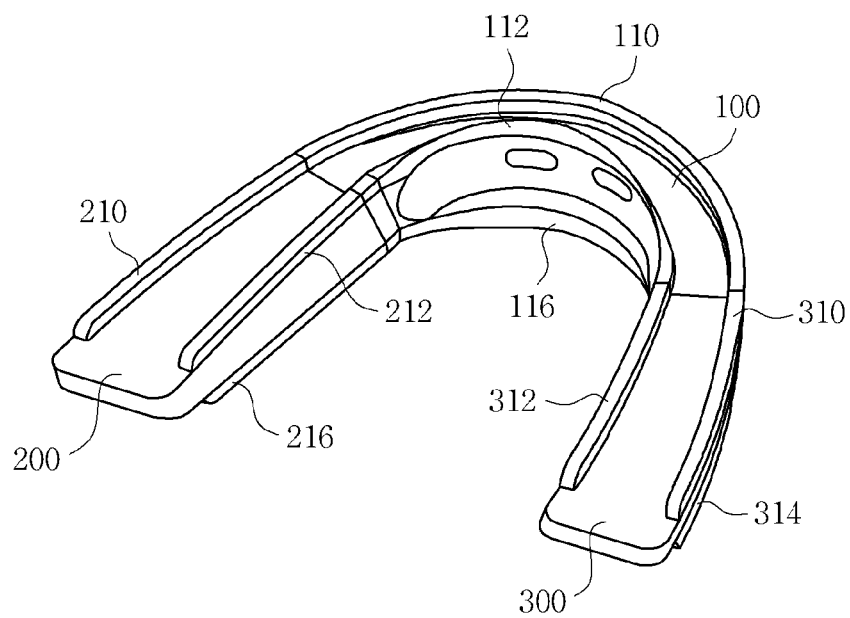
FIG. 1 is a perspective view of a TMJ balancing appliance according to an exemplary embodiment of the present invention.
Figure 2:
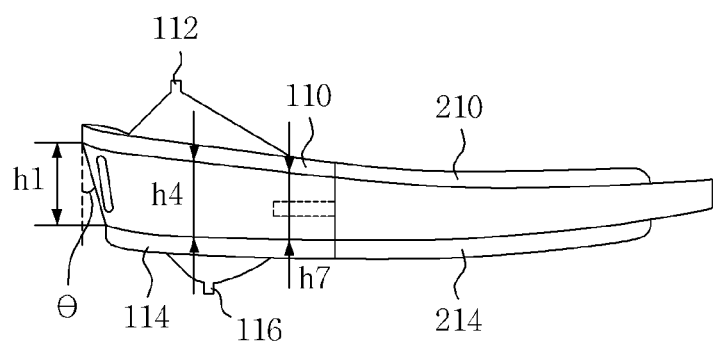
FIG. 2 is a side view of the TMJ balancing appliance illustrated in FIG. 1.

Referring to FIGS. 1 and 2, a TMJ balancing appliance according to an exemplary embodiment of the present invention includes a first base portion 100 for accommodating incisor teeth, a second base portion 200 for accommodating left molar teeth and their adjacent teeth, and a third base portion 300 for accommodating right molar teeth and their adjacent teeth.

The first base portion 100, on which the incisor teeth are mounted, are formed to be higher at a center (height h1) thereof than at opposite sides (height h7) thereof. In an upper part of the first base portion 100, a center (height h2) is highest and opposite sides (height h8) are lower than the center. Also, in a lower part of the first base portion 100, a center (height h3) is highest and opposite sides (height h9) are lower than the center.

Figure 3:
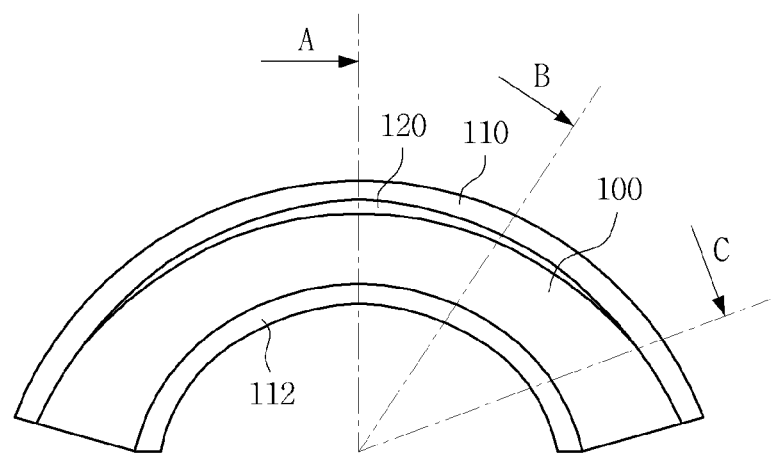
FIG. 3 is a plan view of a first base portion of the TMJ balancing appliance illustrated in FIG. 1.

FIG. 3 is a plan view of the first base portion 100 illustrated in FIG. 1 and FIGS. 4A, 4B and 4C are sectional views of the first base portion 100 illustrated in FIG. 3, taken along A, B and C directions, respectively.

Figure 4:
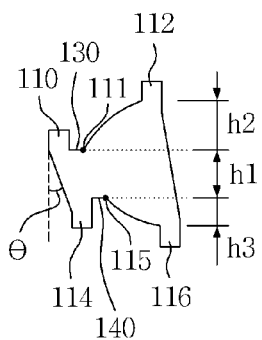
FIGS. 4A, 4B and 4C are sectional views of the first base portion illustrated in FIG. 3, taken along A, B and C directions, respectively.
Figure 4:
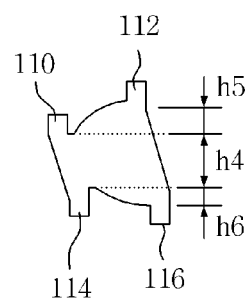
Figure 4:
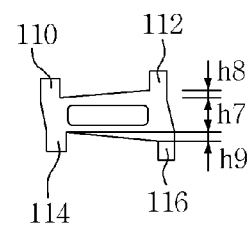
Figure 5:
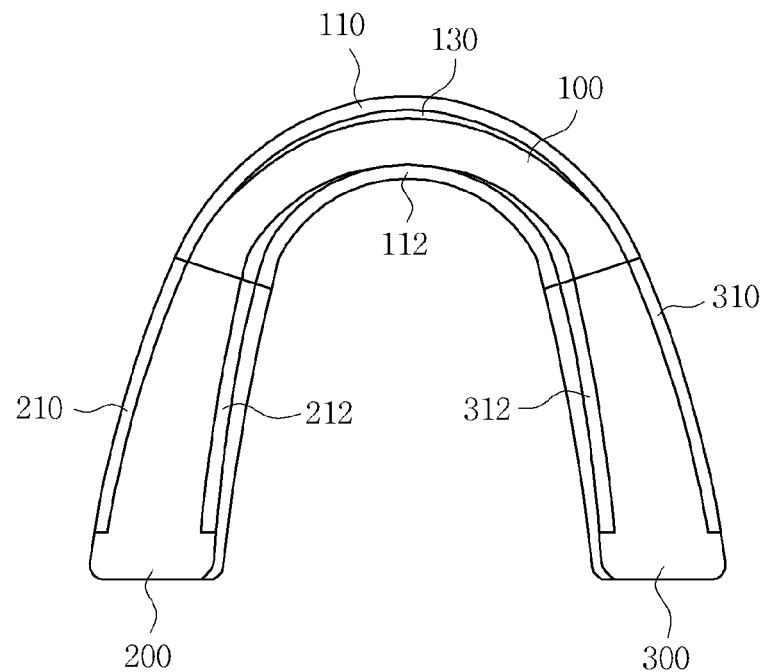
FIG. 5 is a plan view of the TMJ balancing appliance illustrated in FIG. 1.
Figure 6:
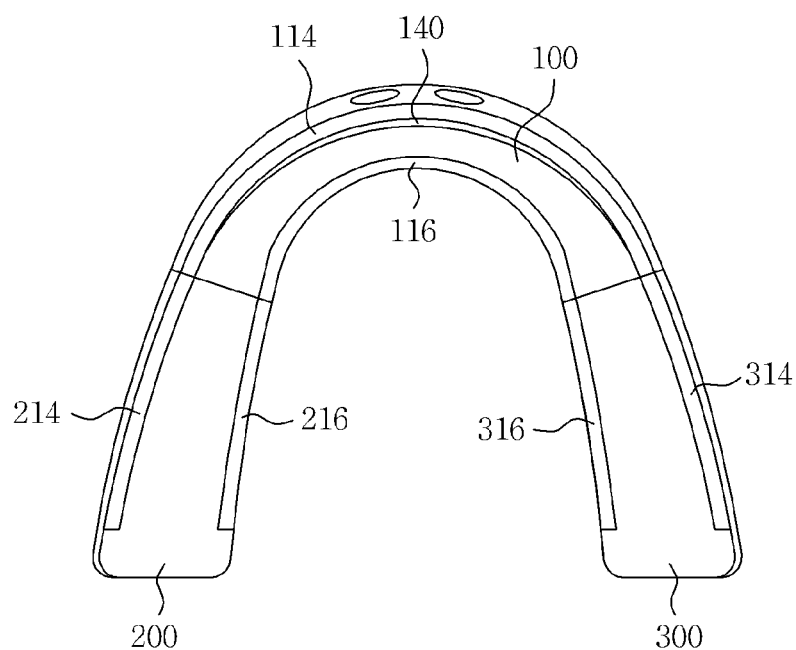
FIG. 6 is a bottom view of the TMJ balancing appliance illustrated in FIG. 1.

Referring to FIGS. 3 to 4C, the height h1 of the center is larger than the height h7 of the opposite sides in the first base portion 100. The first base portion 100 is tapered from the center toward the opposite sides in height (h1>h4>h7). The upper part of the first base portion 100, on which upper teeth are mounted, is highest at the center (height h2) and gets lower at the opposite sides (height h8), thus being tapered from the center toward the opposite sides (h2>h5>h8). Herein, the height of the opposite sides, h8 may be "zero". Similarly, the lower part of the first base portion 100, with which lower teeth are brought into contact, may be formed so that the center is even to the opposite sides or the height gets gradually smaller from the center to the opposite sides. The lower part of the first base portion 100 is highest at the center (height h3) and the opposite sides (height h9) are lower than the center. Also, the lower part of the first base portion 100 is tapered from the center toward the opposite sides in height (h3>h6>h9). The height of the opposite sides, h9 may be 'zero'.

For comfortable accommodation of the upper teeth, the upper part of the first base portion 100 is inclined inward slowly according to normal positions of the upper teeth. Because the upper part of the first base portion 100 gets lower from the center toward the opposite sides, the inclination angle of the center is larger than the inclination angle of the opposite sides and thus the inclination angle gets smaller gradually from the center toward the opposite sides, according to the shapes of the upper teeth. The inclination angle of the opposite sides may be negligibly small so that the opposite sides are almost even.

For comfortable accommodation of the lower teeth, the lower part of the first base portion 100 is inclined inward according to normal positions of the lower teeth. Because the lower part of the first base portion 100 also gets lower from the center toward the opposite sides, the inclination angle of the center is larger than the inclination angle of the opposite sides and thus the inclination angle gets smaller gradually from the center toward the opposite sides, according to the shapes of the lower teeth.

When upper incisor teeth contact lower incisor teeth, the upper incisor teeth are in front of the lower incisor teeth. Based on this occlusion characteristic, the first base portion 100 is inclined inward at an angle θ1 and a starting point 115 of the lower part of the first base portion 100 is behind a starting point 111 of the upper part of the first base portion 100. For example, the lower part starting point 115 may be behind the upper part starting point 111 by 1 to 5 mm.

The first base portion 100 may include at least one of a first upper part outer wall 110 formed along the outer rim of the upper part and a first upper part inner wall 112 formed along the inner rim of the upper part. The first upper part outer wall 110 may be formed along all or part of the outer rim of the upper part, and the first upper part inner wall 112 may be formed along all or part of the inner rim of the upper part.

The first base portion 100 may include at least one of a first lower part outer wall 114 formed along the outer rim of the lower part and a first lower part inner wall 116 formed along the inner rim of the lower part. The first lower part outer wall 114 may be formed along all or part of the outer rim of the lower part, and the first lower part inner wall 116 may be formed along all or part of the inner rim of the lower part.

When a teeth fixing material is filled in the upper part of the first base portion 100, the first upper part inner and outer walls 110 and 112 facilitate easy checking of the filling height of the teeth fixing material and prevent the teeth fixing material from flowing away from the upper part of the first base portion 100. The teeth fixing material is a material which is hardened over a certain time, such as putty, fluid silicon, etc. and which is also elastic to some extent after being hardened to protect the teeth.

When the teeth fixing material is filled in the lower part of the first base portion 100, the first lower part inner and outer walls 114 and 116 facilitate easy checking of the filling height of the teeth fixing material and prevent the teeth fixing material from flowing away from the lower part of the first base portion 100.

The inner and outer walls 110, 112, 114 and 116 are formed to be as low as possible to serve the purposes of preventing flow-away of the teeth fixing material and avoiding contact between the first base portion 100 and gums. For example, the inner and outer walls 110, 112, 114 and 116 may be 0.1 to 5 mm high.

Referring to FIGS. 4A to 6, in order to help to mount the upper teeth comfortably on the upper part of the first base portion 100, a first mounting portion 130 may be formed between the upper part of the first base portion 100 and the first upper outer wall 110. Also, in order to help to mount the lower teeth comfortably on the lower part of the first base portion 100, a second mounting portion 140 may be formed between the lower part of the first base portion 100 and the first lower outer wall 114. The second mounting portion 140 may be longer than the first mounting portion 130.

Figure 7:
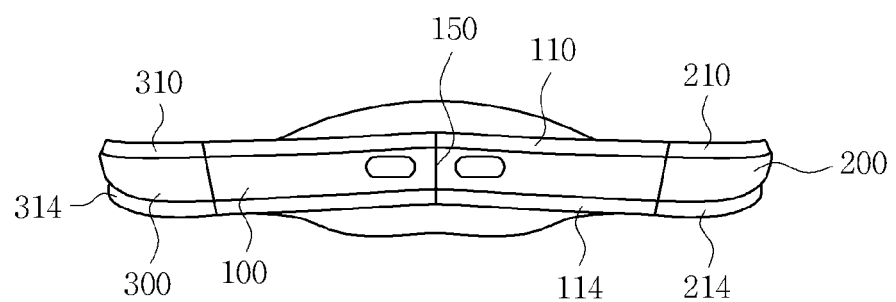
FIG. 7 is a frontal view of the TMJ balancing appliance illustrated in FIG. 1.

Referring to FIG. 7, the first base portion 100 includes a central line 150 with which the incisor teeth are aligned. The central line 150 is formed at the frontal center of the first base portion 100 to easily make sure that when the first base portion 100 is inserted into the mouth, the upper teeth and the lower teeth are aligned with each other in a line.

Figure 8:
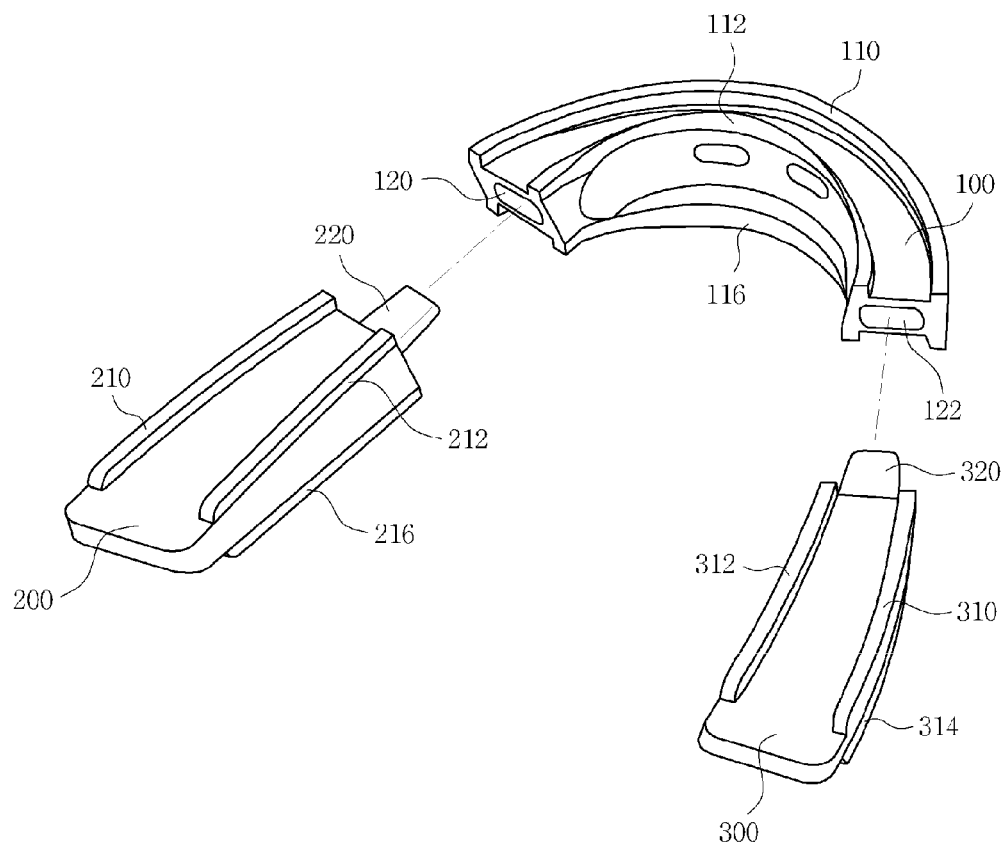
FIG. 8 is an exploded side view of the TMJ balancing appliance illustrated in FIG. 1.

Referring to FIG. 8, the first base portion 100 is provided, at a left side thereof, with a first left engagement portion 120 to be engaged with the second base portion 200 and, at a right side thereof, with a first right engagement portion 122 to be engaged with the third base portion 300.

The second base portion 200 for accommodating the left molar teeth and their adjacent teeth has a second left engagement portion 220 to be engaged with the first left engagement portion 120 at a first side of the first base portion 100. The first and second left engagement portions 120 and 220 function as female and male portions, respectively. When engaged with each other, the first and second left engagement portions 120 and 220 are not detached from each other, whereas they are easily detached from each other when a physical pressure is applied to them.

Figure 9:
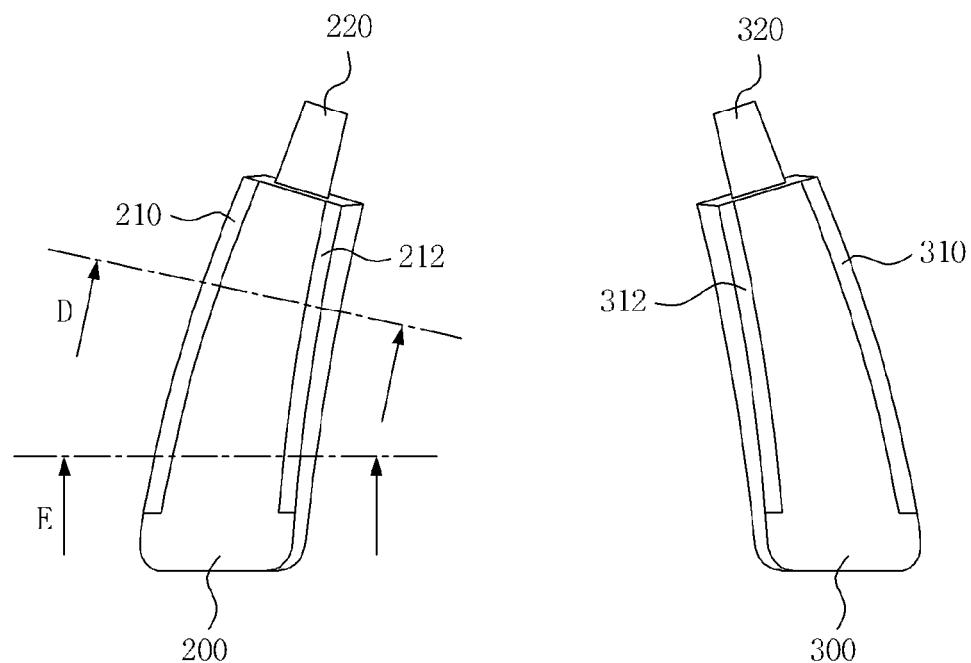
FIG. 9 is a plan view of second and third base portions in the TMJ balancing appliance illustrated in FIG. 1.
Figure 10:
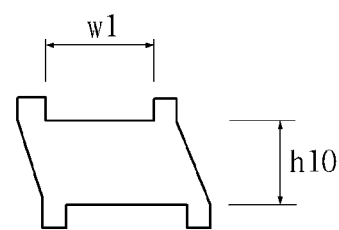
FIGS. 10A and 10B are sectional views of the second base portion illustrated in FIG. 9, taken along D and E directions, respectively.
Figure 10:
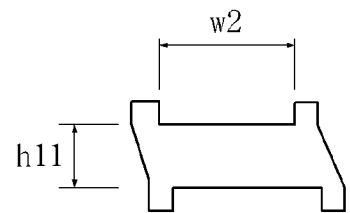

FIG. 9 is a plan view of the second and third base portions and FIGS. 10A and 10B are sectional views of the second base portion, taken along D and E directions.

Referring to FIGS. 9, 10A and 10B, the second base portion 200 gets wider toward an end portion thereof (W1<W2) so that the left molar teeth and their adjacent teeth are mounted comfortably on the second base portion 200. The second base portion 200 is almost even in both frontal and rear parts thereof or slightly higher in the frontal part (height h10) than in the rear part (height h11).

Therefore, the center of the first base portion 100 for accommodating the incisor teeth is thicker than either the second or third base portion 200 or 300 for accommodating molar teeth in the TMJ balancing appliance of the present invention. As the second and third base portions 200 and 300 are lower than the first base portion 100, the molar teeth contact the TMJ balancing appliance than the incisor teeth, to thereby mitigate an impact on the molar teeth that affects a TMJ balance.

The second base portion 200 may include at least one of a second upper part outer wall 210 formed along the outer rim of the upper part and a second upper part inner wall 212 formed along the inner rim of the upper part. The second upper part outer wall 210 may be formed along all or part of the outer rim of the upper part, and the second upper part inner wall 212 may be formed along all or part of the inner rim of the upper part.

The second base portion 200 may include at least one of a second lower part outer wall 214 formed along the outer rim of the lower part and a second lower part inner wall 216 formed along the inner rim of the lower part. The second lower part outer wall 214 may be formed along all or part of the outer rim of the lower part, and the second lower part inner wall 216 may be formed along all or part of the inner rim of the lower part.

The third base portion 300 for accommodating the right molar teeth and their adjacent teeth has a second right engagement portion 320 to be engaged with the first right engagement portion 122 at the second opposite side of the first base portion. The first and second right engagement portions 122 and 320 are symmetrical with the first and second left engagement portions 120 and 220.

The third base portion 300 gets wider toward an end portion thereof so that the right molar teeth and their adjacent teeth are mounted comfortably on the third base portion 300. The third base portion 300 is of the same or almost the same thickness.

The second and third base portions 200 and 300 may be of the same height. Alternatively, considering that when the upper teeth contact the lower teeth, the gap between the right upper and lower molar teeth is wider than the gap between the left upper and lower molar teeth, the third base portion 300 may be formed to be higher than the second base portion 200.

The third base portion 300 may include at least one of a third upper part outer wall 310 formed along the outer rim of the upper part and a third upper part inner wall 312 formed along the inner rim of the upper part. The third upper part outer wall 310 may be formed along all or part of the outer rim of the upper part, and the third upper part inner wall 312 may be formed along all or part of the inner rim of the upper part.

The third base portion 300 may include at least one of a third lower part outer wall 314 formed along the outer rim of the lower part and a third lower part inner wall 316 formed along the inner rim of the lower part. The third lower part outer wall 314 may be formed along all or part of the outer rim of the lower part, and the third lower part inner wall 316 may be formed along all or part of the inner rim of the lower part.

When the teeth fixing material is filled in the upper and lower parts of the second and third base portions 200 and 300, the inner and outer walls of the second and third base portions 200 and 300 facilitate easy checking of the filling height of the teeth fixing material and prevent the teeth fixing material from flowing away from the second and third base portions 200 and 300.

Figure 11:
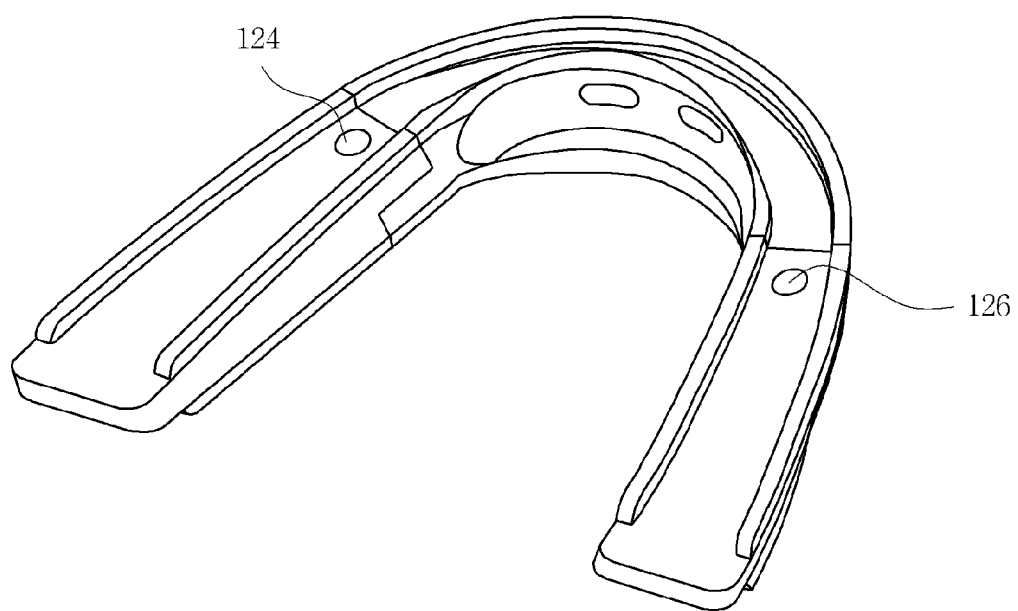
FIG. 11 is a perspective view of a TMJ balancing appliance according to another exemplary embodiment of the present invention.
Figure 12:
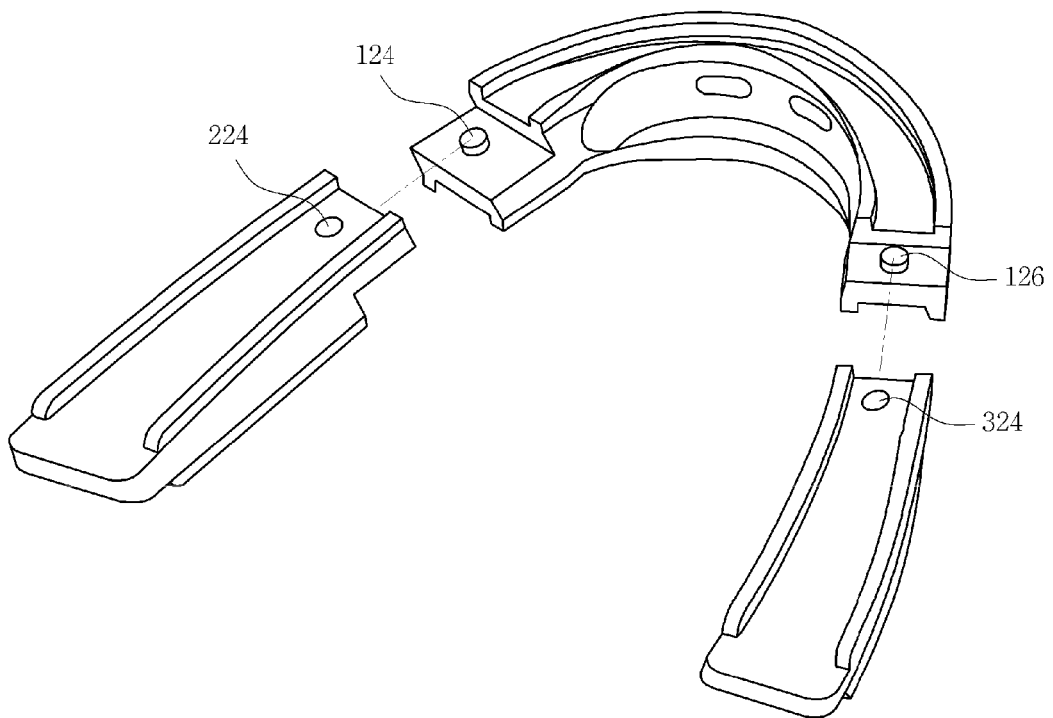
FIG. 12 is an exploded perspective view of the TMJ balancing appliance illustrated in FIG. 11.

FIGS. 11 and 12 are perspective and exploded perspective views of a TMJ balancing appliance according to another exemplary embodiment of the present invention.

Referring to FIGS. 11 and 12, engagement portions are different from those illustrated in FIG. 8 to render the engagement between the first and second (third) base portions 100 and 200 (300) more tight.

Figure 13:
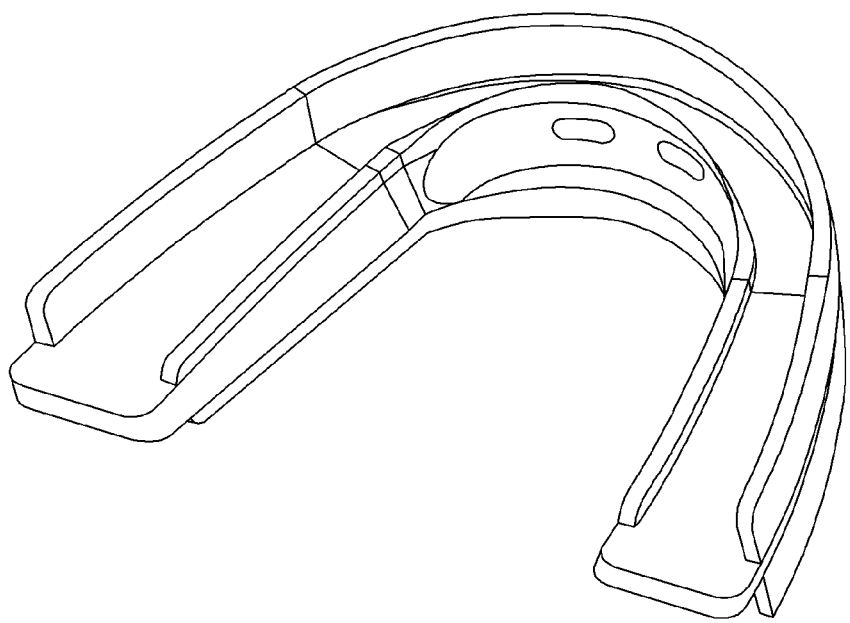
FIG. 13 is a perspective view of a TMJ balancing appliance according to a further exemplary embodiment of the present invention.

FIG. 13 is a perspective view of a TMJ balancing appliance according to a further exemplary embodiment of the present invention.

Referring to FIG. 13, in order to maximize the effect of preventing a teeth deviation and enhance a teeth correction effect, an outer wall (height h2) is as high as an inner wall in the TMJ balancing appliance.

Figure 14:
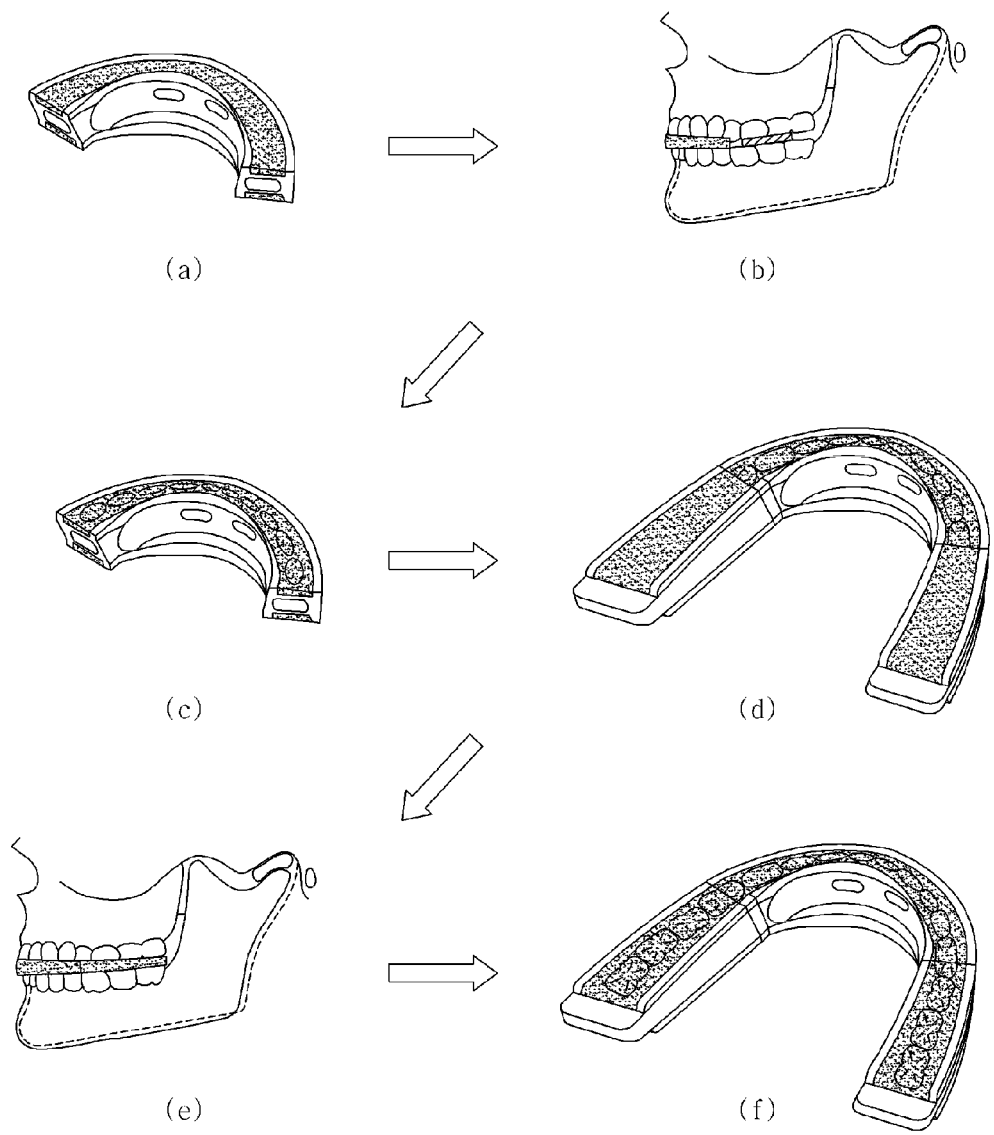
FIG. 14 illustrates a method for using a TMJ balancing appliance according to an exemplary embodiment of the present invention.

With reference to FIG. 14, a method for using a TMJ balancing appliance according to an exemplary embodiment of the present invention will be described in detail.

First of all, left and right balancing bodies are generated to be inserted between left molar teeth and between right molar teeth. The left and right balancing bodies may be formed to a height that gives a feeling of comfort when a user wears them. Since individual users differ in teeth structure and teeth height, the left and right balancing bodies may be of a different height and also, the left and right balancing bodies may be different from each other in height, for each user.

The height of the balancing bodies may be set by measuring the gap between the left molar teeth and the gap between the right molar teeth using a precision measurer. Or, the height of the balancing bodies may be controlled by the user's wearing the balancing bodies between the left molar teeth and between the right molar teeth. Or the balancing bodies may have a predetermined height.

In the case where the user inserts the balancing bodies between the left molar teeth and between the right molar teeth to control the height of the balancing bodies, a measurement sheet of a predetermined thickness may be used as a balancing body in order to facilitate the height control. When the height of the balancing bodies is to be increased, a measurement sheet is added. When the height of the balancing bodies is to be decreased, a measurement sheet is removed. In this manner, the height of the balancing bodies may be controlled accurately. A measurement sheet suffices irrespective of its material, as far as it is 0.05 to 10 mm thick. As its thickness is smaller, the measurement sheet enables a fine height control. For instance, the measurement sheet may be formed of paper, vinyl, cellophane, silicon, etc.

The height of the balancing bodies may be set based on the horizontal and vertical balances of the TMJ, to thereby enhance the effect of protecting the TMJ. The vertical balance means that the left and right jaw joins are horizontal with respect to the head. The differences between a horizontal balance point and the left and right position of the jaw joints may be set as the heights of the balancing bodies. The vertical balance means that the jaw joints are at upper and lower centers with respect to the head. Final heights of the balancing bodies may be determined based on the heights of the balancing bodies determined by the horizontal balance and the differences between a vertical balance point and the upper and lower positions of the jaw joints.

Subsequently, the left and right balancing bodies are inserted between the left molar teeth and between the right molar teeth and the shapes of the incisor teeth are molded into a first base portion in which a teeth fixing material is filled.

To be more specific, the teeth fixing material is filled to a predetermined height on the upper and lower surfaces of the first base portion. Then with the upper and lower teeth opened, the first base portion filled with the teeth fixing material is placed on the lower incisor teeth of the user and the left and right balancing bodies are inserted between the left molar teeth and between the right molar teeth, respectively. Then the upper and lower teeth are brought into natural contact so that the left and right molar teeth contact the left and right balancing bodies, respectively. If teeth occlusion is performed using the central line of the first base portion for left and right alignment between the upper and lower incisor teeth, the effect of TMJ protection is enhanced.

After the teeth fixing material is hardened to a certain strength, the first base portion is removed from the incisor teeth, thus obtaining a resultant structure in which the shapes of the upper and lower incisor teeth are molded.

The resultant structure serves as a fixing frame for the incisor teeth so that the gap between the left upper and lower molar teeth becomes the height of the left balancing body and the gap between the right upper and lower molar teeth becomes the height of the right balancing body.

Then second and third base portions are engaged with the first base portion in which the shapes of the incisor teeth are molded and the shapes of the other teeth are molded in the second and third base portions filled with the teeth fixing material using the first base portion.

More specifically, the second and third base portions are engaged with the first base portion having the shapes of the incisor teeth molded therein. Then the teeth fixing material is filled to a predetermined height on the upper and lower surfaces of the second and third base portions. Then with the upper and lower teeth opened, the first base portion with the shapes of the incisor teeth molded therein is placed on the lower incisor teeth of the user and the upper and lower teeth are brought into natural contact. After the teeth fixing material is hardened to a certain strength, the second and third base portions are removed from the user, thus obtaining a final resultant structure in which the shapes of the upper and lower teeth are molded.

The gap between the left upper and lower molar teeth becomes the height of the left balancing body and the gap between the right upper and lower molar teeth becomes the height of the right balancing body. Thus the TMJ balancing appliance with the shapes of the teeth of the user molded in the upper and lower parts thereof is finally produced.

In accordance with a method for using a TMJ balancing appliance according to another exemplary embodiment of the present invention, if the left and right balancing bodies are to be made as high as the second and third base portions, the first base portion is engaged with the second and third base portions, the teeth fixing material is filled to a predetermined height in the upper and lower parts of the first, second and third base portions, the first, second and third base portions are placed in compliance with the shapes of the teeth, with the upper and lower teeth opened from each other, and then the upper and lower teeth are brought into natural contact. After the teeth fixing material is hardened to a certain strength, the first, second and third base portions are removed from the teeth of the user, thus obtaining a final resultant structure in which the shapes of the user's teeth are molded.

Therefore, the gap between the left upper and lower molar teeth becomes the height of the left base portion and the gap between the right upper and lower molar teeth becomes the height of the right base portion. Thus the TMJ balancing appliance with the shapes of the teeth of the user molded in the upper and lower parts thereof is finally produced.

As is apparent from the above description, the exemplary embodiments of the present invention balances a TMJ, thus minimizing TMJ imbalances, inducing relaxation of muscles related to the TMJ and activating circulation of cerebrospinal fluid.

Since the height of a part in which molar teeth are brought into contact can be controlled and a TMJ balancing appliance can be customized to meet an individual's teeth structure, a TMJ balance can be maintained more accurately. Therefore, TMJ imbalances are eliminated and the effect of TMJ balance is maximized.

Further, the TMJ balancing appliance is designed so that molar teeth being a core of TMJ balancing contact the TMJ balancing appliance earlier than other teeth. Therefore, TMJ imbalances are eliminated. When the TMJ balancing appliance is worn, incisor teeth contact normally, thus increasing a comfortable wearing feeling of a user.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. A TemporoMandibular Joint (TMJ) balancing apparatus comprising:
 a first base portion configured to receive incisor teeth, the first base portion having a first engagement portion and a second engagement portion;
 a second base portion configured to receive left molar teeth, the second base portion having a third engagement portion; and
 a third base portion and configured to receive right molar teeth, the third base portion having a fourth engagement portion,
 wherein the first base portion includes an upper part and a lower part to receive upper incisor teeth and lower incisor teeth, respectively, and has a height which tapers from a central region toward the left side and the right side of the first base portion,
 wherein a left side and a right side of the first base portion are detachably coupled to the second base portion and the third base portion, respectively, by engaging the first engagement portion of the first base portion with the third engagement portion of the second base portion and by engaging the second engagement portion of the first base portion with the fourth engagement portion of the third base portion, and
 wherein the first base portion is inclined inward and a starting point of the lower part of the first base portion is behind a starting point of the upper part of the first base portion.

2. The TMJ balancing apparatus of claim 1, wherein the first base portion includes at least one of the upper part outer wall formed along the upper part outer rim of the first base portion, an upper part inner wall formed along an upper part inner rim of the first base portion, the lower part outer wall formed along the lower part outer rim of the first base portion, and a lower part inner wall formed along a lower part inner rim of the first base portion.

3. The TMJ balancing apparatus of claim 2, wherein the second base portion includes at least one of an upper part outer wall formed along an upper part outer rim of the second base portion, an upper part inner wall formed along an upper part inner rim of the second base portion, a lower part outer wall formed along a lower part outer rim of the second base portion, and a lower part inner wall formed along a lower part inner rim of the second base portion.

4. The TMJ balancing apparatus of claim 2, wherein the third base portion includes at least one of an upper part outer wall formed along an upper part outer rim of the third base portion, an upper part inner wall formed along an upper part inner rim of the third base portion, a lower part outer wall formed along a lower part outer rim of the third base portion, and a lower part inner wall formed along a lower part inner rim of the third base portion.

5. The TMJ balancing apparatus of claim 1, wherein the upper part of the first base portion has an inclined portion on which the upper incisor teeth are mounted, the inclined portion having an inclination angle which decreases from the central region to the left and right sides of the first base portion.

6. The TMJ balancing apparatus of claim 1, wherein the lower part of the first base portion has an inclined portion on which the lower incisor teeth are mounted, the inclined portion having an inclination angle which decreases from the central region to the left and right sides of the first base portion.

7. The TMJ balancing apparatus of claim 1, wherein the first base portion includes a first mounting portion between the upper part of the first base portion and an upper part outer wall of the first base station, and a second mounting portion between the lower part of the first base portion and a lower part outer wall of the first base station.

8. The TMJ balancing apparatus of claim 1, wherein the second mounting portion is longer than the first mounting portion.

9. The TMJ balancing apparatus of claim 1, wherein the first base portion is higher than the second and third base portions.

10. The TMJ balancing apparatus of claim 1, wherein the third base portion is higher than the second base portion.

11. The TMJ balancing apparatus of claim 1, wherein the first base portion includes a central line by which to make sure whether incisor teeth are aligned with a frontal center of the first base portion.

12. The TemporoMandibular Joint (TMJ) balancing apparatus of claim 1,
 wherein the first base portion has an outer wall formed along an outer rim of the first base station, and an inner wall formed along an inner rim of the first base station and the outer wall is higher than the inner wall.

13. A method for manufacturing a TemporoMandibular Joint (TMJ) balancing apparatus, comprising:
- generating a left balancing body and a right balancing body so as to determine a gap between left molar teeth and a gap between right molar teeth, respectively;
- generating a first base portion filled with a teeth fixing material so as to mold shapes of incisor teeth, the first base portion having a left side and a right side; and
- generating a second base portion and a third base portion filled with a teeth fixing material so as to mold shapes of the left molar and right molar teeth, respectively,
- wherein the left side and the right side of the first base portion have the same heights as the left balancing body and the right balancing body, respectively,
- wherein the second base portion and the third base portion have different heights, and
- wherein the teeth fixing material is filled in at least one of upper and lower parts of the first base portion.

14. The method of claim 13, wherein the teeth fixing material is filled in at least one of upper parts of the second and third base portions and lower parts of the second and third base portions.

15. The method of claim 13, wherein generating the first base portion further comprises:
- placing the first base portion filled with the teeth fixing material on incisor teeth of a user;
- inserting the left and right balancing bodies between the upper and lower left molar teeth and between the upper and lower right molar teeth; and
- molding the shapes of the incisor teeth by closing upper and lower teeth so that the left and right molar teeth contact the left and right balancing bodies, respectively.

16. The method of claim 13, wherein generating the second and third base portions further comprises:
- combining the first base portion having the shapes of the incisor teeth molded therein with the second and third base portions;
- filling the teeth fixing material to a predetermined height on surfaces of upper and lower parts of the second and third base portions;
- fixing the first base portion having the shapes of the incisor teeth molded therein over the incisor teeth, while upper and lower teeth are opened; and
- molding the shapes of the left and right molar teeth by closing the upper and lower teeth.

* * * * *